United States Patent [19]

Khan et al.

[11] E Patent Number: Re. 33,408

[45] Reissued Date of Patent: Oct. 30, 1990

[54] PROCESS FOR LPG RECOVERY

[75] Inventors: Shuaib A. Khan; James Haliburton, both of Calgary, Canada

[73] Assignee: Exxon Production Research Company, Houston, Tex.

[21] Appl. No.: 809,666

[22] Filed: Dec. 16, 1985

Related U.S. Patent Documents

Reissue of:

[64] Patent No.: 4,507,133
Issued: Mar. 26, 1985
Appl. No.: 537,127
Filed: Sep. 29, 1983

[51] Int. Cl.[5] ..... F25J 3/02

[52] U.S. Cl. ..... 62/29; 62/31; 62/43

[58] Field of Search ..... 62/23, 24, 27, 28, 29, 62/30, 32, 31, 34, 36, 38, 39, 42, 43, 44, 9, 11

[56] References Cited

U.S. PATENT DOCUMENTS

| | | | |
|---|---|---|---|
| 3,312,073 | 4/1967 | Jackson et al. | 62/9 |
| 3,675,435 | 7/1972 | Jackson et al. | 62/39 |
| 3,724,226 | 4/1973 | Pachaly | 62/39 |
| 3,932,156 | 1/1976 | Stern | 62/17 |
| 4,070,165 | 1/1978 | Colton | 62/17 |
| 4,140,504 | 2/1979 | Campbell et al. | 62/28 |
| 4,272,269 | 6/1981 | Hammond et al. | 62/39 |

OTHER PUBLICATIONS

Drawing 83-4306-020-001; Rev O; Imperial Oil Limited; 1974.

Drawing 4-003 c; Rev O; The Fluor Corporation; 5/16/73.

*Primary Examiner*—Frank Sever

*Attorney, Agent, or Firm*—James H. Riley; Richard F. Phillips

[57] ABSTRACT

An improved process is described for the separation and recovery of substantially all the propane and heavier hydrocarbon components in a hydrocarbon gaseous feedstream. In this process, the vapor stream from a deethanizer is cooled to liquefaction and contacted with a vapor phase from the hydrocarbon gaseous feedstream. The contact takes place within a direct heat exchanger, and the resulting vapor fraction, which is essentially ethane and methane, is the gaseous product of the process.

41 Claims, 3 Drawing Sheets

PROCESS FOR LPG RECOVERY

Matter enclosed in heavy brackets [ ] appears in the original patent but forms no part of this reissue specification; matter printed in italics indicates the additions made by reissue.

FIELD OF THE INVENTION

This invention relates to a process for treating a gaseous hydrocarbon containing feedstream such as natural gas, crude oil solution gas or refinery gas to separate and recover propane and heavier hydrocarbon components.

BACKGROUND OF THE INVENTION

Gaseous streams containing methane and ethane occur naturally, such as in natural gas and crude oil solution gas, and also as byproducts of a variety of refinery processes. In addition to methane and ethane, these gases often contain a substantial quantity of hydrocarbons of higher molecular weight, e.g., propane, butane, pentane and their unsaturated analogs.

Recent substantial increases in the market for the propane and heavier hydrocarbon components of natural gas have provided demand for process yielding higher recovery levels of these products. Available processes for separating these materials include those based upon cooling and refrigeration of gas, oil absorption, refrigerated oil absorption, and the more recent cryogenic process utilizing the principle of gas expansion through a mechanical device to produce power while simultaneously extracting heat from the system. Depending upon the pressure of the gas source, the richness (propane and heavier hydrocarbon content) of the gas and the desired end results, each of these prior art processes or a combination thereof may be employed.

Prior to the advent of the cryogenic expansion process, propane and the heavier component hydrocarbons were frequently separated by liquefaction and treatment with an absorption medium. The natural gas streams were contacted with an absorption oil (usually heptane), and the propane and the heavier hydrocarbon components were absorbed and thereafter desorbed and recovered.

In most present day refining processes, propane and the higher molecular weight components of natural gas and refinery gas are separated and recovered by liquefaction and cryogenic distillation at temperatures below 0° F. Refrigeration for separation is supplied totally or partially by expansion of the gaseous stream in a turboexpander which produces power that may be used for example in driving a compressor.

In a typical cryogenic expansion-type recovery process, a feedstream gas under pressure is cooled by heat exchange with other streams of the process and/or external sources of cooling such as a propane compression refrigeration system. As the gas is cooled, liquids are condensed and are collected in one or more separators as a high pressure liquid feed containing most of the desired propane and heavier hydrocarbons. The high pressure liquid feed is transferred to a deethanizer column after its pressure is adjusted to the operating pressure of the deethanizer. The deethanizer is a fractionating column in which the liquid feed is fractionated to separate residual methane and ethane from the desired produces of propane and heavier hydrocarbon components.

If the feedstream is not totally condensed (typically it is not), the vapor remaining from this partial condensation is expanded in a turboexpander to a lower pressure. Additional liquids are condensed as a result of the further cooling of the stream during expansion. The pressure after the expansion is usually the same pressure at which the deethanizer is operated. Liquids thus obtained are also supplied as a feed to the deethanizer. Typically, remaining vapor and deethanizer overhead vapor are combined as a residual methane/ethane product gas.

In the ideal operation of such a separation process, the vapors leaving the process will contain substantially all the methane and ethane found in the feed gas to the recovery plant and substantially no propane or heavier hydrocarbon components. The bottoms fraction leaving the deethanizer will contain substantially all the propane and heavier hydrocarbon components and essentially no methane or ethane. In practice, this ideal situation is not obtained because the conventional deethanizer is operated largely as a stripping column. Therefore, the methane and ethane vapors leaving the top fractionation stage of the column will contain vapors not subjected to any rectification step. Substantial losses of propane and heavier hydrocarbons occur because the vapors discharged from the low temperature separation steps contain propane and heavier hydrocarbon components which could be recovered if those vapors were brought to lower temperature, or if they were contacted with a significant quantity of a relatively heavy hydrocarbon, e.g. heptane, capable of absorbing the propane.

U.S. Pat. No. 4,272,269 which issued to Hammond, et al on June 6, 1981 described one such process that combines both the cryogenic expansion step and the absorption process to increase the recovery percentage of the propane and hydrocarbon components. The disadvantage with using an absorption oil is that additional refining steps are needed to desorb the propane and prepare the absorption oil for reuse.

The problem associated with all types of propane recovery operations is one of efficiency. The main objective is to recover as much of the propane and heavier hydrocarbon components as is economically possible. The conventional systems in operation today are capable of economically recovering, at most, about 95% of the propane in a feedstream. Because of the large volume of gas that is processed, there is a definite need to find efficient methods to recover more of the propane and heavier hydrocarbons in a gaseous feedstream.

SUMMARY OF THE INVENTION

The present invention relates to a process for treating a gaseous hydrocarbon-containing feedstream where it is desirable to leave substantially all of the methane and ethane in the hydrocarbon gaseous stream and to separate and recover substantially all of the propane and heavier hydrocarbon components. It has been found that increased percentage of propane and heavier hydrocarbon components can be economically recovered by contacting the expanded vapor from a gaseous feedstream with at least a portion of the liquefaction overhead from a deethanizer.

The process of the present invention comprises cooling a gaseous hydrocarbon-containing feedstream to form a vapor stream and a liquid stream. The liquid stream is transferred to a deethanizer while the vapor stream is expanded transferred to the bottom of a direct heat exchanger column. The deethanizer overhead, which consists mainly of methane and ethane, is cooled liquefaction and fed to the upper portion of the direct heat exchanger column. The liquid methane and ethane flow downward within the direct heat exchanger column and contact gaseous propane and heavier hydrocarbons that flow upward. The methane and ethane vaporize by absorbing heat from the gaseous propane and heavier hydrocarbons which causes the propane and heavier hydrocarbons to condense at the bottom of the direct heat exchanger column. The gaseous methane and ethane within the direct heat exchanger column are removed from the overhead as a product of the process. The liquid at the bottom of the direct heat exchanger column is removed and fed to the lower portion of the deethanizer. The liquid at the bottom of the deethanizer is removed as a product of the process, and at least a portion of the gaseous overhead is cooled and returned to the top of the direct heat exchanger column.

DETAILED DESCRIPTION OF THE INVENTION

According to the present invention, a gaseous feedstream of natural gas, solution gas or refinery gas, which typically contains hydrocarbons ranging from methane to hexane, is processed to separate and recover the propane and heavier hydrocarbon components.

Figure 1:
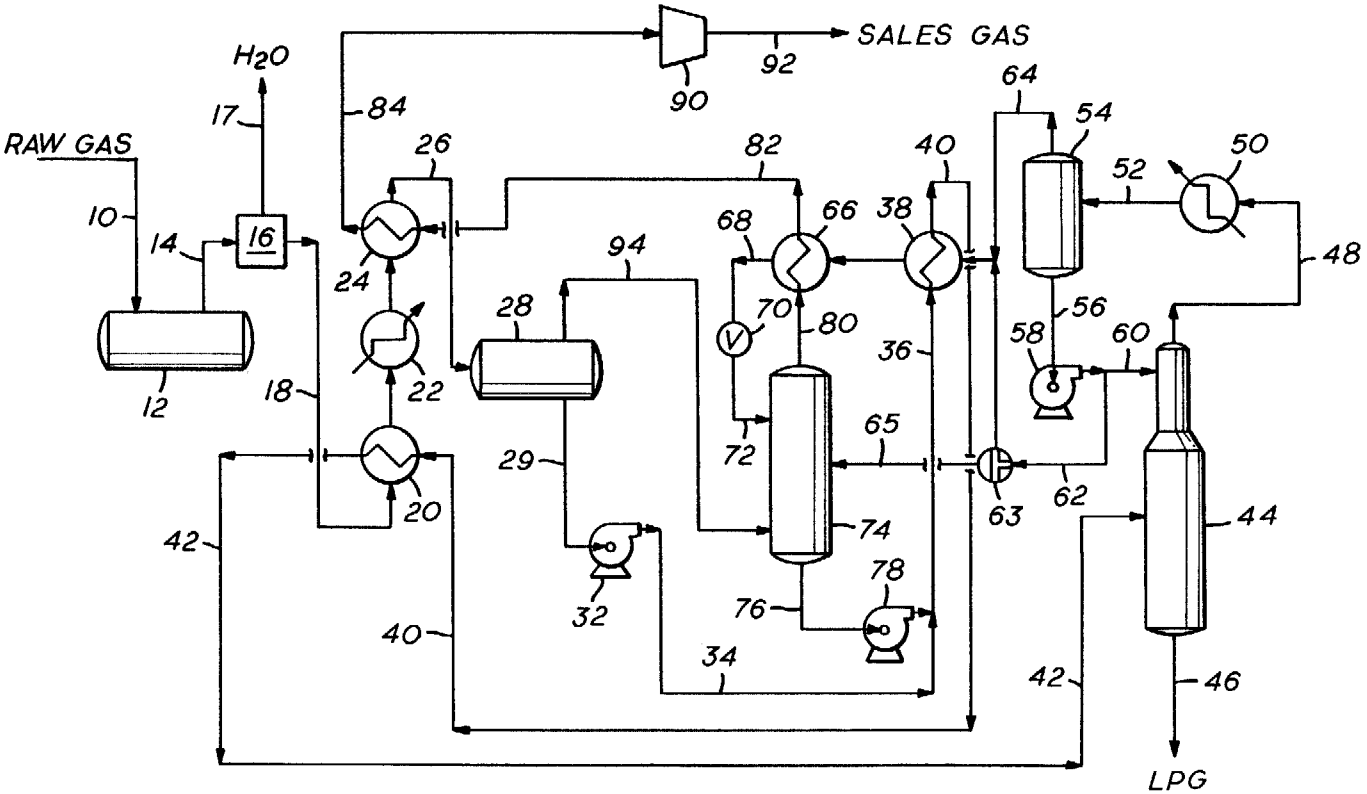
FIG. 1 is a schematic flow diagram illustrating the present invention.

As illustrated in FIG. 1, the gaseous feedstream comes in through line 10. The natural gas feed to a natural gas plant will generally be at about atmospheric temperature and at an elevated pressure substantially above atmospheric pressure. Prior to the initial cooling step, the gaseous feedstream enters an inlet separator 12 for removal of liquid hydrocarbons. Additionally, water vapor in the feedstream is removed in a dehydration unit 16 to avoid the formation of ice throughout the process. These preparatory steps are known to those skilled in the art and, depending on the composition of the gaseous feedstream, may not be necessary.

The gaseous feedstream flows through line 18 and is initially cooled to a temperature of about −10° F. One method of cooling the feedstream, as shown in FIG. 1, involves contact with indirect heat exchangers 20 and 24 and a propane refrigerant 22. Other methods are available and known to those skilled in the art. After the gaseous feedstream is sufficiently cooled, it enters an inlet vessel 28 where it is separated into a vapor stream and a liquid stream. The vapor stream is expanded and passes through line 94 into the lower portion of a direct heat exchanger column 74 which is a mixing chamber. Direct heat exchanger column 74 may have a variety of configurations, but its purpose is to allow direct contact between vapor and liquid phases. A packed column is one configuration that can function as a direct heat exchanger. A preferred configuration is similar to a tray-type absorber where liquid enters the top and flows down a series of trays, contacting gas which is flowing upward from the bottom.

Figure 2:
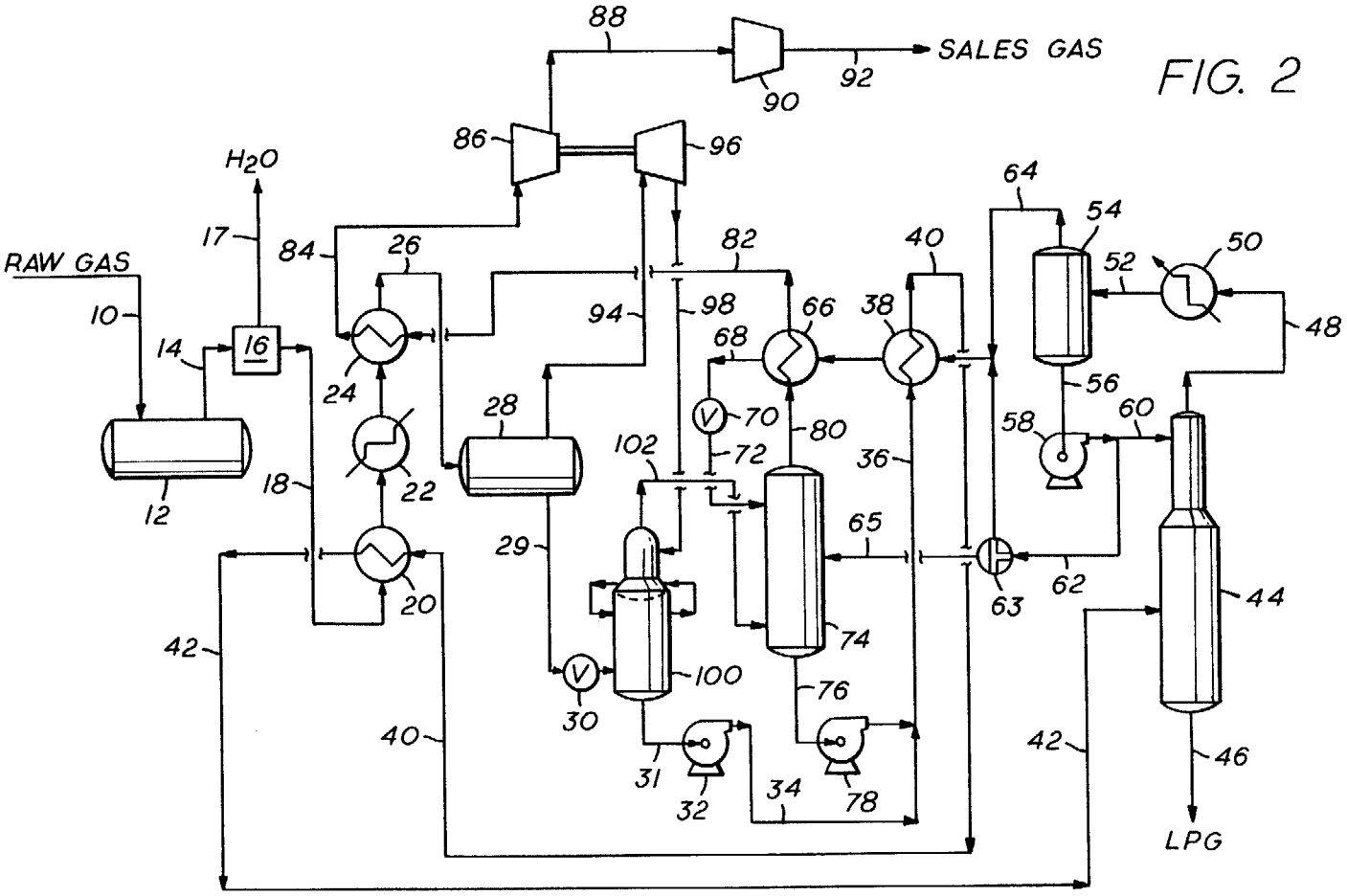
FIG. 2 is a schematic flow diagram illustrating a preferred embodiment of the present invention.

FIG. 2 represents a preferred embodiment where the vapor stream from inlet vessel 28 is work expanded in turboexpander 96, cooled to a temperature of about −50° F. and partially condensed. This cooled and partially condensed stream flows through line 98 to the upper portion of a separator 100. The liquid from the inlet vessel 28 flowing through line 29 passes through an expansion valve 30 and enters the lower portion of separator 100. The liquid from the bottom of the separator 100 combines with the liquid from the direct heat exchanger column 74 in line 36. The vapor from separator 100 is fed to the lower portion of the direct heat exchanger column 74.

This preferred embodiment is most effective on gaseous feedstreams rich in propane and heavier hydrocarbon components. The additional steps separate many of these components early in the process, thus increasing the efficiency of the subsequent separation steps.

Referring to FIG. 2, the flow from line 102 into the lower portion of the direct heat exchanger column 74 contains gaseous propane and heavier hydrocarbon components. These gases flow upward, contacting downward flowing liquid methane and ethane which enter the upper portion of the direct heat exchanger column through line 72 (described in more detail later). The liquid methane and ethane descend from tray to tray in the direct heat exchanger column and evaporate. The energy for the evaporization is supplied by the condensation of gaseous propane and heavier hydrocarbons ascending from the bottom of the direct heat exchanger column.

A vapor stream consisting essentially of pure methane and ethane is formed within the direct heat exchanger column 74. The overhead from the direct heat exchanger column flows through line 80, passes through a series of indirect heat exchangers 66 and 24, and enters the compressor side 86 of the turboexpander. After this compression step, the gas is further compressed in a residual gas compressor 90 and is removed as a gaseous product of the process.

The liquid propane and heavier hydrocarbons are removed from the bottom of the direct heat exchanger column 74 through line 76 and combined with the liquid stream from separator 100. These streams are heated through a series of indirect heat exchangers and can provide some or all of the cooling requirement for gas entering inlet vessel 28. The warmed liquid stream is fed to the deethanizer 444 which is essentially a fractionating column. Liquid from the bottom of the deethanizer 44 is removed through line 46 as a liquid product of the process. The liquid product consists essentially of propane and heavier hydrocarbon components.

The gaseous overhead from the deethanizer is cooled and fed to the direct heat exchanger column 75. FIG. 2 shows one embodiment where the deethanizer overhead, which consists essentially of methane and ethane, is cooled by propane refrigeration 50 and fed to separator 54. The liquid portion flows out line 56. Part of the liquid is returned through line 60 to the deethanizer as reflux, and the rest of it flows through line 62 into line 64. Alternatively, line 62 can flow into the direct heat exchanger column 74. In either case, vapor in line 64 is further cooled by indirect heat exchangers 38 and 66 to about −50° F. at which point the vapor liquefies. The liquid flows through line 68 to an expansion valve 70 where the methane and ethane is partially flashed, further reducing the temperature to about −70° F. After the pressure reduction, the cold liquid and gas flow through line 72 into the upper portion of the direct heat exchanger column 74. The cycle is complete with the liquid methane and ethane descending from tray to tray condensing gaseous propane and heavier hydrocarbons and the gaseous methane and ethane flowing out the top of the direct heat exchanger column through line 80.

Figure 3:
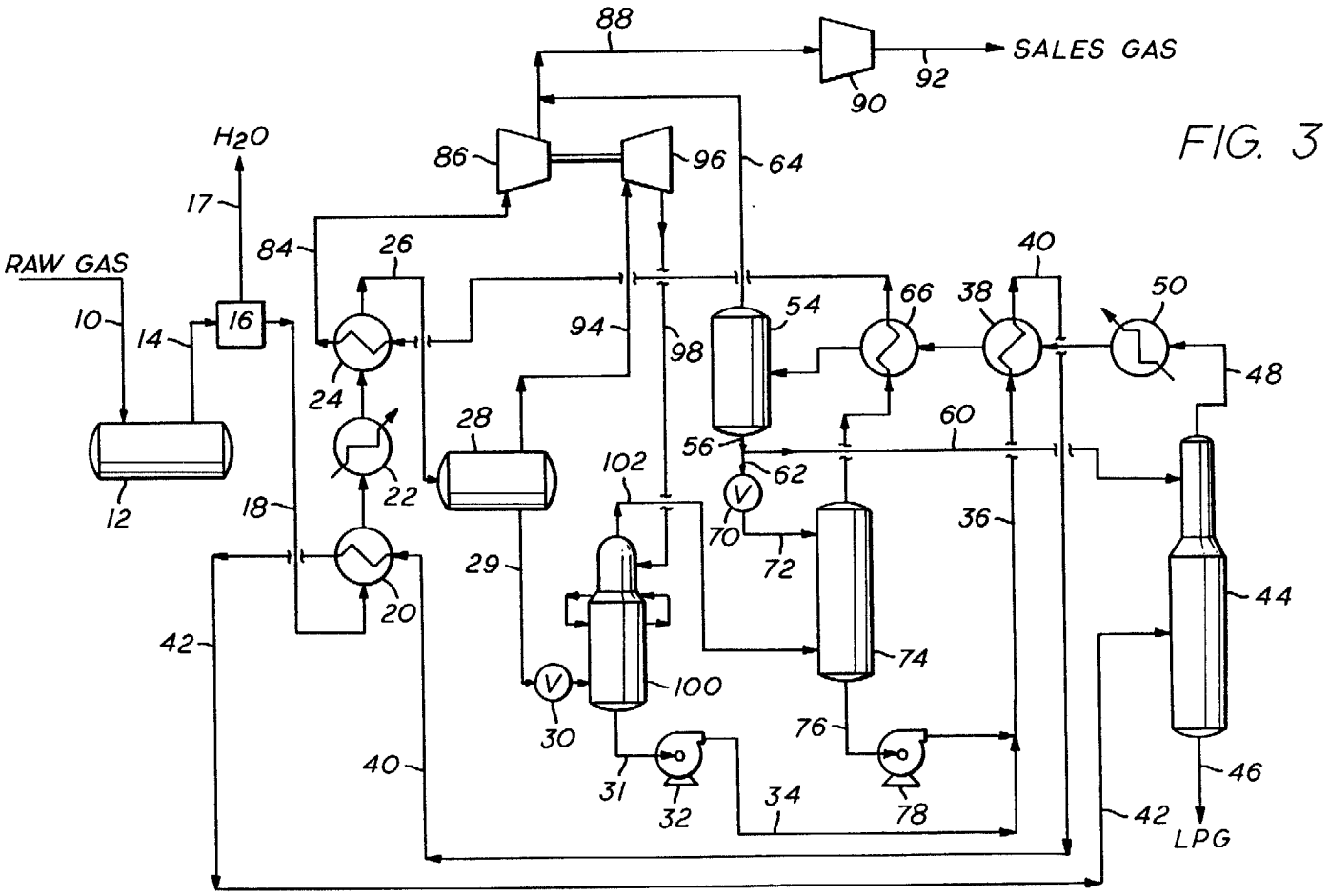
FIG. 3 is a schematic flow diagram illustrating a variation of the preferred embodiment of the present invention.

FIG. 3 shows an embodiment where some of the deethanizer overhead is removed from the process. In this embodiment, the deethanizer overhead is cooled by propane refrigerant 50 and indirect heat exchangers 38 and 66 prior to entering separator 54. The gaseous overhead from separator 54 has little, if any, propane and heavier hydrocarbons. The overhead is transferred to line 88 through line 64, and the liquid flows out through line 56. Part of the liquid is returned through line 60 to the deethanizer as reflux, and the rest flows through expansion valve 70, partially flashing the methane and ethane. As previously stated, the flow from line 72 is fed to the upper portion of the direct heat exchanger unit, and the liquid methane and ethane descend from tray to tray condensing gaseous propane and heavier hydrocarbons.

EXAMPLE

The process of this invention will be further understood by reference to a specific example. For illustrative purposes, a gaseous feedstream having the following composition will be used:

| Component | Mole % |
|---|---|
| Carbon Dioxide | .900 |
| Nitrogen | 3.540 |
| Hydrogen Sulfide | 0.000 |
| Methane | 65.043 |
| Ethane | 19.353 |
| Propane | 7.376 |
| I-Butane | 0.835 |
| Butane | 2.121 |
| I-Pentane | 0.321 |
| Pentane | 0.320 |
| Hexane+ | 0.191 |

By way of illustration, the gaseous feedstream in this instance would be at a temperature of about 70° F. and a pressure of about 515 psia.

The following table illustrates the calculated temperatures and pressures at major points as the feedstream passes through the system shown in FIG. 2.

| Line or Unit Number | Temperature °F. | Pressure psia |
|---|---|---|
| 26 | −10.00 | 500 |
| 34 | −26.21 | 300 |
| 102 | −41.58 | 300 |
| 80 | −71.00 | 300 |
| 76 | −55.00 | 300 |
| 42 | 48.00 | 490 |
| 48 | 47.10 | 490 |
| 64 | 24.04 | 485 |
| 60 | 24.04 | 490 |
| 62 | 24.04 | 490 |
| 72 | −73.83 | 300 |
| 84 | 53.00 | 285 |
| 46 | 215.00 | 490 |

The composition of the gaseous product of the process from the direct heat exchanger column 74 passing through line 80 and the liquid product of the process from the deethanizer passing through line 46 would be as follows:

| Component | Mole % |
|---|---|
| Gaseous Product Composition (80) | |
| Carbon Dioxide | 1.014 |
| Nitrogen | 3.987 |
| Hydrogen Sulfide | 0.000 |
| Methane | 73.269 |
| Ethane | 21.595 |
| Propane | 0.133 |
| I-Butane | 0.000 |
| Butane | 0.000 |
| I-Pentane | 0.000 |
| Pentane | 0.000 |
| Hexane+ | 0.000 |
| Liquid Product Composition (46) | |
| Carbon Dioxide | 0.000 |
| Nitrogen | 0.000 |
| Hydrogen Sulfide | 0.000 |
| Methane | 0.000 |
| Ethane | 1.627 |
| Propane | 64.639 |
| I-Butane | 7.437 |
| Butane | 18.890 |
| I-Pentane | 2.857 |
| Pentane | 2.845 |
| Hexane+ | 1.702 |

By way of comparison, the recovery of propane in conventional systems is about 95 mol % of feedstream, whereas this process separates and recovers about 98 to 99 mol % of the propane in the feedstream.

The principle of the invention and the best mode contemplated for applying that principle have been described. It is to be understood that the foregoing is illustrative only and that other means and techniques can be employed without departing from the true scope of the invention defined in the following claims.

We claim:

1. In a process for separating propane and heavier hydrocarbons from a gaseous feedstream containing hydrocarbon components of different boiling points wherein said feedstream is cooled and separated into a first vapor fraction and a first liquid fraction and said first liquid fraction is distilled in a deethanizer to form a second vapor fraction and a second liquid fraction, the improvement which comprises [expanding and] transferring said first vapor fraction to the lower portion of a direct heat exchanger, cooling *at least a portion of* said second vapor fraction *by passing it through an indirect heat exchanger* to form a substantially liquefied stream, *partially flashing at least a portion of said liquefied stream and transferring* [at least a portion of said liquefied stream] *it* to the upper portion of said direct heat exchanger whereby said liquefied stream contacts said first vapor fraction to form a third vapor fraction and a third liquid fraction, [returning] *transferring* said third liquid fraction to said deethanizer, [and] removing said third vapor fraction from said direct heat exchanger *and passing said third vapor fraction through said indirect heat exchanger.*

2. A process as described in claim 1 wherein said direct heat exchanger is a packed column.

3. A process as described in claim 1 wherein said direct heat exchanger is a tray column.

4. A process as described in claim 1, [wherein] *further comprising expanding* said first vapor fraction [is expanded] in a turboexpander *prior to transferring it to the lower portion of said direct heat exchanger.*

[5. A process as described in claim 1 further comprising partially flashing said liquefied stream prior to transferring it to said direct heat exchanger.]

6. A process for separating propane and heavier hydrocarbons from a gaseous feedstream containing hydrocarbon components of different boiling points which comprises:

(a) cooling and separating said feedstream into a first vapor fraction and a first liquid fraction;

(b) distilling said first liquid fraction [is] *in* a deethanizer to form a second vapor fraction and a second liquid fraction;

(c) removing said second liquid fraction from said deethanizer as a liquid product;

(d) [expanding said first vapor fraction and] transferring [it] *said first vapor fraction* to the lower portion of a direct heat exchanger;

(e) cooling said second vapor fraction to form a third vapor fraction and a third liquid fraction;

(f) returning at least a portion of said third liquid fraction to said deethanizer as reflux;

(g) [further] cooling said third vapor fraction to form a [substantially liquefied] stream *which is at least partially liquefied;*

(h) [transferring] *partially flashing at least a portion of* said liquefied stream *and transferring it* to the upper portion of said direct heat exchanger whereby said liquefied stream contacts said first vapor fraction to form a fourth vapor fraction and a fourth liquid fraction;

(i) removing said fourth vapor fraction from said direct heat exchanger [as a gaseous product]; and (j) [returning] *transferring* said fourth liquid fraction to said deethanizer.

7. A process as described in claim 6 wherein said direct heat exchanger is a packed column.

8. A process as described in claim 6 wherein said direct heat exchanger is a tray column.

9. A process as described in claim 6 [wherein] *further comprising expanding* said first vapor fraction [is expanded] in a turboexpander *prior to transferring it to the lower portion of said direct heat exchanger.*

[10. A process as described in claim 6 further comprising partially flashing said liquefied stream prior to transferring it to said direct heat exchanger.]

11. A process as described in claim 6 further comprising combining at least a portion of said third liquid fraction with said third vapor fraction prior to [further] cooling said third vapor fraction.

12. A process as described in claim 6 further comprising transferring at least a portion of said third liquid fraction to said direct heat exchanger.

13. A process for separating propane and heavier hydrocarbons from a gaseous feedstream containing hydrocarbon components of different boiling points which comprises:

(a) cooling and separating said feedstream into a first vapor fraction and a first liquid fraction;

(b) distilling said first liquid fraction in a deethanizer to form a second vapor fraction and a second liquid fraction;

(c) removing said second liquid fraction from said deethanizer as a liquid product;

(d) [expanding said first vapor fraction and] transferring [it] *said first vapor fraction* to the lower portion of a direct heat exchanger;

(e) cooling said second vapor fraction to form a third vapor fraction and a third liquid fraction;

(f) removing said third vapor fraction as a gaseous product;

(g) returning 171 at least] a *first* portion of said third liquid fraction to said deethanizer as reflux;

(h) [transferring at least] *partially flashing* a *second* portion of said third liquid fraction *and transferring it* to the upper portion of said direct heat exchanger whereby said *second portion of said* third liquid fraction contacts said first vapor fraction to form a fourth vapor fraction and a fourth liquid fraction;

(i) removing said fourth vapor fraction from said direct heat exchanger [as a gaseous product]; and (j) transferring said fourth liquid fraction to said deethanizer.

14. A process as described in claim 13 wherein said direct heat exchanger is a packed column.

15. A process as described in claim 13 wherein said direct heat exchanger is a tray column.

16. A process as described in claim 13 [wherein] *further comprising expanding* said first vapor fraction [is expanded] in a turboexpander *prior to transferring it to the lower portion of said direct heat exchanger.*

[17. A process as described in claim 13 further comprising partially flashing said third liquid fraction prior to transferring it to said direct heat exchanger.]

*18. The process as set forth in claim 1 wherein said second vapor fraction is cooled and separated into a fourth vapor fraction and a fourth liquid fraction upon removal from said distilling unit, said fourth vapor fraction constituting said portion of said second vapor fraction.*

*19. The process as set forth in claim 1 wherein said distilling unit is maintained at a substantially higher pressure than said direct heat exchanger.*

*20. The process as set forth in claim 18 wherein said distilling unit is maintained at a substantially higher pressure than said direct heat exchanger.*

*21. The process as set forth in claim 1 wherein said first vapor fraction and said first liquid fraction are passed through a separator prior to being transferred to said direct heat exchanger and said deethanizer, respectively.*

*22. The process as set forth in claim 6 wherein said deethanizer is maintained at a substantially higher pressure than said direct heat exchanger.*

*23. The process as set forth in claim 23 wherein said first vapor fraction and said first liquid fraction are passed through a separator prior to being transferred to said direct heat exchanger and said deethanizer, respectively.*

*24. The process as set forth in claim 22 wherein the step of cooling said third vapor fraction includes transferring heat from said third vapor fraction to said fourth liquid fraction.*

*25. The process as set forth in claim 13 wherein said deethanizer is maintained at a substantially higher pressure than said direct heat exchanger.*

*26. The process as set forth in claim 25 wherein said first vapor fraction and said first liquid fraction are passed through a separator prior to being transferred to said direct heat exchanger and said deethanizer, respectively.*

*27. A process for separating methane and ethane from the heavier components of a hydrocarbon feedstream, comprising the steps of:*

*(a) separating said feedstream into a first vapor fraction and a first liquid fraction;*

*(b) transferring said first vapor fraction to a direct heat exchanger;*

(c) transferring said first liquid fraction to a distilling unit;

(d) distilling the fluids introduced into said distilling unit to yield a second vapor fraction and a second liquid fraction;

(e) cooling and separating said second vapor fraction into a third layer fraction and a third liquid fraction;

(f) returning at least a portion of said third liquid fraction to said distilling unit;

(g) passing said third vapor fraction through an indirect heat exchanger to liquefy at least a portion of said third vapor fraction;

(h) decreasing the pressure of said at least partially liquefied third vapor fraction, whereby at least a portion of the liquid phase flashes;

(i) transferring said partially liquefied third vapor fraction to said direct heat exchanger whereby said partially liquefied third vapor fraction mixes with said first vapor fraction, yielding a fourth vapor fraction and fourth liquid fraction;

(j) transferring said fourth liquid fraction to said distilling unit whereby said fourth liquid fraction is distilled with said first liquid fraction; and, (k) removing said fourth vapor fraction from said direct heat exchanger and passing it through said indirect heat exchanger to transfer heat from said third vapor fraction to said fourth vapor fraction.

28. The process as set forth in claim 27 wherein said distilling unit is maintained at a substantially higher pressure than said indirect heat exchanger.

29. The process as set forth in claim 28 wherein said first vapor fraction is expanded in a turboexpander prior to transfer to said direct heat exchanger.

30. The process as set forth in claim 27 further comprising the step of transferring heat from said third vapor fraction to said fourth liquid fraction prior to step (g).

31. The process as set forth in claim 27 wherein said distilling unit is a deethanizer.

32. The process as set forth in claim 27 wherein said first vapor fraction and said first liquid fraction are passed through a separator prior to being transferred to said direct heat exchanger and said distilling unit, respectively.

33. A process for separating methane and ethane from the heavier components of a hydrocarbon feedstream, comprising the steps of:

(a) separating said feedstream into a first vapor fraction and a first liquid fraction;

(b) transferring said first vapor fraction to a direct heat exchanger;

(c) transferring said first liquid fraction to a distilling unit;

(d) distilling the fluids introduced into said distilling unit to yield a second vapor fraction and a second liquid fraction;

(e) passing said second vapor fraction through a first indirect heat exchanger to cool it;

(f) separating said cooled second vapor fraction into a third vapor fraction and a third liquid fraction;

(g) returning at least a first portion of said third liquid fraction to said distilling unit;

(h) partially flashing a second portion of said third liquid fraction and transferring it to said direct heat exchanger whereby said partially flashed second portion of said third liquid fraction contacts said first vapor fraction to establish a fourth vapor fraction and a fourth liquid fraction;

(i) transferring said fourth liquid fraction to said distilling unit whereby said fourth liquid fraction is distilled with said first liquid fraction; and, (j) removing said fourth vapor fraction from said direct heat exchanger and passing it through said indirect heat exchanger to transfer heat from said second vapor fraction to said fourth vapor fraction.

34. The process as set forth in claim 33 wherein said distilling unit is maintained at a substantially higher pressure than said indirect heat exchanger.

35. The process as set forth in claim 34 wherein said first vapor fraction is expanded in a turboexpander prior to transfer to said direct heat exchanger.

36. The process as set forth in claim 33 wherein step (e) includes transferring heat from said second vapor fraction to said fourth liquid fraction.

37. The process as set forth in claim 33 wherein said distilling unit is a deethanizer.

38. The process as set forth in claim 33 wherein said third and fourth vapor fractions are removed as the gas product of the process and said second liquid fraction is removed as the liquid product of the process, said gas product being substantially free from propane and heavier hydrocarbons and said liquid product being substantially free from methane and ethane.

39. The process as set forth in claim 33 wherein said first vapor fraction and said first liquid fraction are passed through a separator prior to being transferred to said direct heat exchanger and said distilling unit, respectively.

40. A process for separating a hydrocarbon feedstream into a first portion predominantly composed of methane and ethane, and a second portion predominantly composed of propane and heavier hydrocarbons, said process comprising the steps of:

(a) cooling and separating said feedstream into a first vapor fraction and a first liquid fraction;

(b) expanding said first vapor fraction and transferring it to a direct heat exchanger;

(c) transferring said first liquid fraction to a deethanizer, said deethanizer being effective to convert the fluids introduced therein into a second vapor fraction and a second liquid fraction, said deethanizer being maintained at a higher pressure than said direct heat exchanger;

(d) removing said second liquid fraction as a product predominantly composed of propane and heavier hydrocarbons;

(e) removing and cooling said second vapor fraction to yield a third vapor fraction and a third liquid fraction;

(f) returning at least a portion of said third liquid fraction to said deethanizer;

(g) passing said third vapor fraction through an indirect heat exchanger to remove heat from and liquefy at least a portion of said third vapor fraction;

(h) decreasing the pressure of said third vapor fraction to flash at least a portion of the liquefied gases within said third vapor fraction whereby said third vapor fraction is further cooled;

(i) introducing said third vapor fraction into said direct heat exchanger, whereby said third vapor fraction and said first vapor fraction come into contact to form a fourth vapor fraction and a fourth liquid fraction;

(j) removing said fourth vapor fraction as a product predominantly composed of methane and ethane;

(k) passing said fourth vapor fraction through said indirect heat exchanger to transfer heat from said third vapor fraction to said fourth vapor fraction; and

*(l) transferring said fourth liquid fraction to said deethanizer.*

*41. The process as set forth in claim 40 wherein the expansion of step (b) is conducted in a turboexpander.*

*42. The process as set forth in claim 40 further including the step of passing said third vapor fraction and said fourth liquid fraction through a second indirect heat exchanger to transfer heat from said third vapor fraction to said fourth liquid fraction.*

*43. The process as set forth in claim 40 wherein said first vapor fraction and said first liquid fraction are passed through a separator prior to being transferred to said direct heat exchanger and said deethanizer, respectively.*

*44. The process as set forth in claim 40 wherein at least a portion of said third liquid fraction is added to said third vapor fraction prior to passing said third vapor fraction through said indirect heat exchanger.*

* * * * *